United States Patent [19]

Heath et al.

[11] Patent Number: 4,732,756

[45] Date of Patent: Mar. 22, 1988

[54] (Z)-3-DODECEN-1-OL (E)-2-BUTENOATE AND ITS USE IN MONITORING AND CONTROLLING THE SWEETPOTATO WEEVIL

[75] Inventors: Robert R. Heath; James A. Coffelt, both of Gainesville, Fla.; Fredrick I. Proshold, St. Croix, V.I.; Philip E. Sonnet, Doylestown, Pa.; James H. Tumlinson, III, Gainesville, Fla.

[73] Assignee: The United States of America as represented by the Secretary of Agriculture, Washington, D.C.

[21] Appl. No.: 879,696

[22] Filed: Jun. 27, 1986

[51] Int. Cl.[4] .................... A01N 25/00; C07C 69/56
[52] U.S. Cl. .................................. 424/84; 514/549; 560/225
[58] Field of Search ................ 560/225; 514/549; 424/84

[56] References Cited

PUBLICATIONS

J. A. Coffelt, K. W. Wick, L. L. Sower, and W. T. McClennan, "Sex Pheromone of the Sweetpotato Weevil, *Cylas formicarius elegantus*: Laboratory Bioassay and Evidence of a Multiple Component System", *Environmental Entomology*, 7(5): 756–758 (1978).

R. G. Brownlee and R. M. Silverstein, "A Micro-Preparative Gas Chromatograph and a Modified Carbon Skeleton Determinator", *Analytical Chemistry*, 40(13): 2077–2079 (1968).

R. R. Heath and R. E. Doolittle, "Derivatives of Cholesterol Cinnamate: A Comparison of the Separations of Geometric Isomers When Used as Gas Chromatographic Stationary Phases", *Journal of High Resolution Chromatography*, 6: 16–19 (1983).

M. Beroza and B. A. Bierl, "Rapid Determination of Olefin Position in Organic Compounds in Microgram Range by Ozonolysis and Gas Chromatography", *Analytical Chemistry*, 39(10): 1131–1135 (1967).

R. Mozingo, "Palladium Catalysts", *Organic Syntheses*, 3: 685–690 (1955).

Primary Examiner—Donald B. Moyer
Assistant Examiner—L. Hendriksen
Attorney, Agent, or Firm—M. Howard Silverstein; David G. McConnell; Margaret A. Connor

[57] ABSTRACT

A pheromonal compound produced by the sweetpotato weevil has been identified as (Z)-3-dodecen-1-ol (E)-2-butenoate. The synthetically-prepared compound demonstrates activity toward the sweetpotato weevil comparable to or greater than that of the natural female and comparable to that of its natural counterpart under field conditions. The novel compound provides a sensitive tool for detection of the sweetpotato weevil. By attracting adult weevils to field traps, this compound provides a means for monitoring and controlling this major agricultural pest.

9 Claims, 9 Drawing Figures

(Z)-3-DODECEN-1-OL (E)-2-BUTENOATE AND ITS USE IN MONITORING AND CONTROLLING THE SWEETPOTATO WEEVIL

BACKGROUND OF THE INVENTION

1. Field of the Invention

This invention relates to a novel compound and use thereof to monitor and control the sweetpotato weevil. More particularly, the invention relates to (Z)-3-dodecen-1-ol (E)-2-butenoate and its use as an attractant, disruptant, and monitoring agent for the sweetpotato weevil.

2. Description of the Art

Sweet potato is considered the sixth most important human food crop in the world and is surpassed in importance as a root crop only by the potato. The sweetpotato weevil, *Cylas formicarius elegantulus* (Summers), is the most devastating pest of sweet potatoes worldwide. Even very low level pre- and postharvest infestations reduce both quality and marketable yield and can render the sweet potato unfit for consumption. This is due to the presence of extremely bitter tasting and toxic sesquiterpenes that are produced by the sweet potato tissue in response to insect feeding and that impart a bitter taste to the sweet potato. Losses due to such infestations and diseases that often follow weevil attack are estimated at 35 to 95%.

Presently, there is no suitable method available for the detection of low level infestations; by the time insects are seen on the crop, considerable damage has already been done. The underground feeding habits of the sweetpotato weevil larvae and the nocturnal activity of the adults make it difficult for farmers to make effective use of pesticides. Thus, there is a need for a sensitive detection tool to aid the grower in monitoring and controlling infestations of this major agricultural pest.

The use of insect sex attractants as potential control agents in integrated pest management programs has been reported. A number of economically important insects are currently monitored, partially controlled, or completely controlled by use of their own specific sex pheromone. The use of pheromones has also been reported for locating, surveying, or monitoring pest populations at levels not otherwise detectable. In the case of the sweetpotato weevil, the lack of identification and availability of a sweetpotato weevil pheromone has precluded application of this technology to the treatment of this pest.

SUMMARY OF THE INVENTION

We have now for the first time obtained in pure or substantially pure form the major female-produced sex attractant of the sweetpotato weevil, *Cylas formicarius elegantus* (Summers). This new compound, identified as (Z)-3-dodecen-1-ol (E)-2-butenoate, has been isolated from females of the sweetpotato weevil (SPW) and has also been successfully synthesized.

The novel compound of the invention is the first crotonate ester identified as an insect sex attractant. The synthetic material demonstrates biological activity toward SPW males comparable to or greater than that of the natural SPW female and comparable to that of the purified natural attractant. (Z)-3-dodecen-1-ol (E)-2-butenoate is highly effective in attracting SPW males to traps baited with the compound.

The novel compound provides a sensitive tool for detection of the SPW and provides a means for population control and population density estimation of this pest. Its usefulness in eliciting a behavioral response when applied to a locus of SPW males suggests the following economic applications: (1) the detection of infestation outbreaks; (2) the monitoring of existing adult populations in order to predict future infestation levels for scheduling treatment with conventional pesticides; and (3) the control of reproduction in adult populations either by direct disruption of mating through confusing or inhibitory properties, or by attracting a demographically significant portion of the male population for subsequent destruction or sterilization.

In accordance with this discovery it is an object of the invention to identify for the first time a unique sex attractant for the sweetpotato weevil.

It is also an object of the invention to provide a mean for the production of synthetic (Z)-3-dodecen-1-ol (E)-2-butenoate.

Another object of the invention is to utilize (Z)-3-dodecen-1-ol (E)-2-butenoate as a detection, monitoring, or control agent for this major agricultural pest.

A further object is to provide a SPW sex attractant for use with insecticides, biological control agents and the like to attract and combat the pest.

Other objects and advantages of the invention will become readily apparent from the ensuing description.

DETAILED DESCRIPTION OF THE INVENTION

Figure 1:
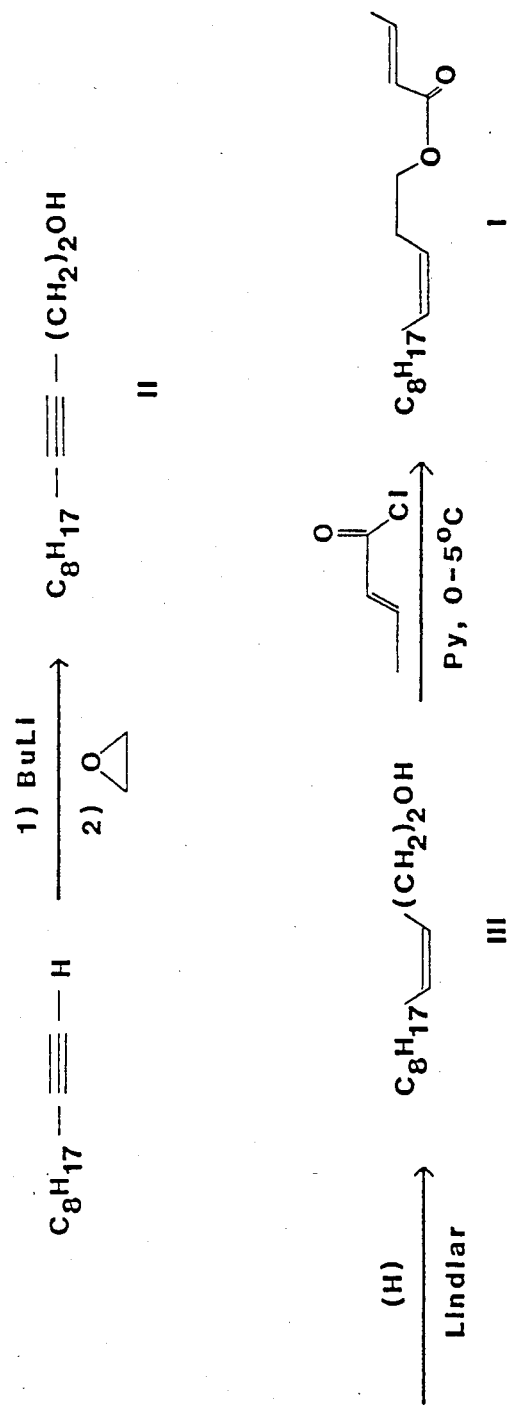
FIG. 1 shows the synthesis of (Z)-3-dodecen-1-ol (E)-2-butenoate.

The novel sex attractant compound of the invention, (Z)-3-dodecen-1-ol (E)-2-butenoate is characterized by the following structural formula:

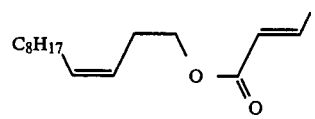

The novel compound was isolated from volatiles of SPW females following a sequence of four chromatographic separations: (1) silica (gravity flow), (2) high performance liquid chromatography (HPLC), (3) gas-liquid chromatography (GLC) using a nonpolar (methyl silicone stationary phase) column, and (4) GLC using a polar (polyethylene glycol stationary phase) column. The novel sex attractant compound also can be prepared synthetically as described in Example 2 below and shown in FIG. 1. As used in the specification and the claims, the phrase "pure or substantially pure" mean that the novel compound of the invention is substantially free of undesirable masking or inhibitory effects with regard to the intended activity, and in cases where it is obtained from SPW volatiles, it has been purified following the sequence of four chromatographic procedures described above or by procedures providing equivalent purity.

The biological and chemical data show that (Z)-3-dodecen-1-ol (E)-2-butenoate is the major component of the female produced sex pheromone of the SPW (*C. f. elegantulus*). Unlike pheromone components that have been described for many Coleoptera species, the material functions as a sex pheromone in that it is produced by one sex, and elicits an overt series of behaviors (activation, orientation, etc.) only by the opposite sex.

ISOLATION OF THE ATTRACTANT

To obtain the active compound in pure or substantially pure form from the insect volatiles, a lengthy sequence of complex chromatographic procedures was carried out. The complete details of the isolation procedure are described in Example 1 below. Briefly, the insect volatiles were obtained by drawing air over SPW females and collecting the volatiles on an adsorbent continuously over a 30-day period for a given batch of insects. The concentrated volatile fraction which contained in excess of several thousand compounds, was then chromatographed on silica (gravity flow). The active fractions from the gravity flow column were concentrated and chromatographed by HPLC. The active fractions eluted from the HPLC column were combined, concentrated, and further purified by GLC on a nonpolar methyl silicone (OV-101) column. The active fraction obtained from the OV-101 GLC column contained in excess of 400 compounds. The material required still further purification by GLC using a polar polyethylene glycol (Carbowax) column.

Beginning with the unpurified volatiles (crude extract) and continuing through the purification, all material (combined, active, and inactive fractions) were bioassayed in serial dilution (6–10 replicates per dose) in the laboratory (FIG. 2A) to ensure that no loss in activity had occurred. In addition, field bioassays of the crude extract, the HPLC purified material, and the Carbowax GLC purified material were conducted to ensure that no loss of activity in the field occurred as a result of the separation performed. Results of these field bioassays at equal dose are summarized in FIG. 2B. The dilution series obtained for the gravity flow silica column and for the micropreparative GLC samples from the nonpolar column and the inactive fractions are omitted from FIG. 2 for simplicity. For all comparisons, there was no indication of loss of biological activity in either field or laboratory bioassays.

All biological activity of the active material that was obtained from the HPLC column followed by further purification by GLC on a packed methyl silicone (OV-101) column was contained within a 2-min fraction with a Kovat's Index (KI) of 1780–1800 (Kovats, 1965). No increase or decrease in biological activity was observed when the active fraction was recombined with other GLC fractions and subsequently bioassayed over a range of $1 \times 10^{31\ 4}$ to $1 \times 10^{-1}$ female equivalent days (FED) in the laboratory.

Figure 2A:
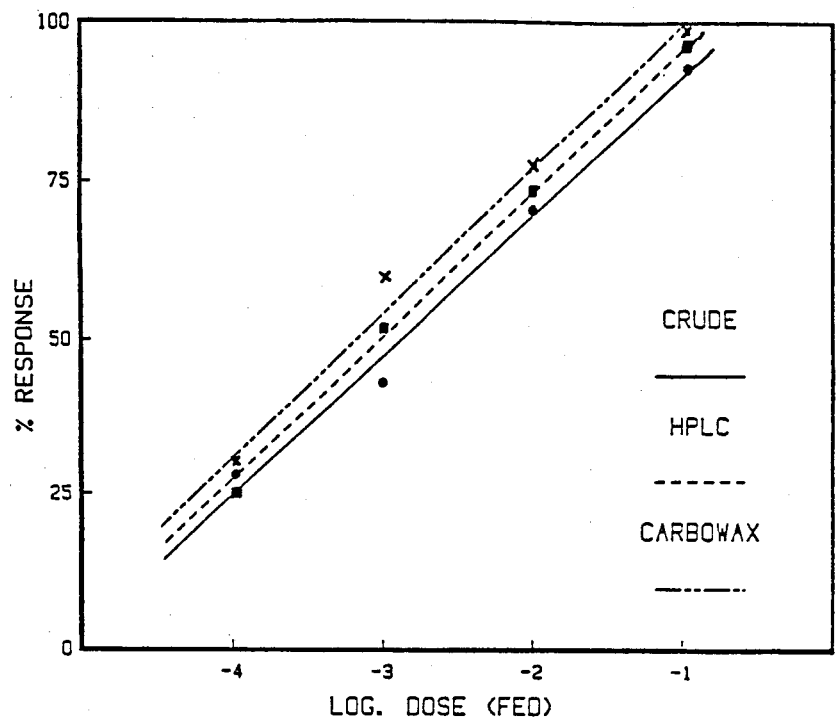
FIGS. 2A and 2B show the laboratory (A) and field (B) response of the SPW to various isolates containing (Z)-3-dodecen-1-ol (E)-2-butenoate.
Figure 2B:
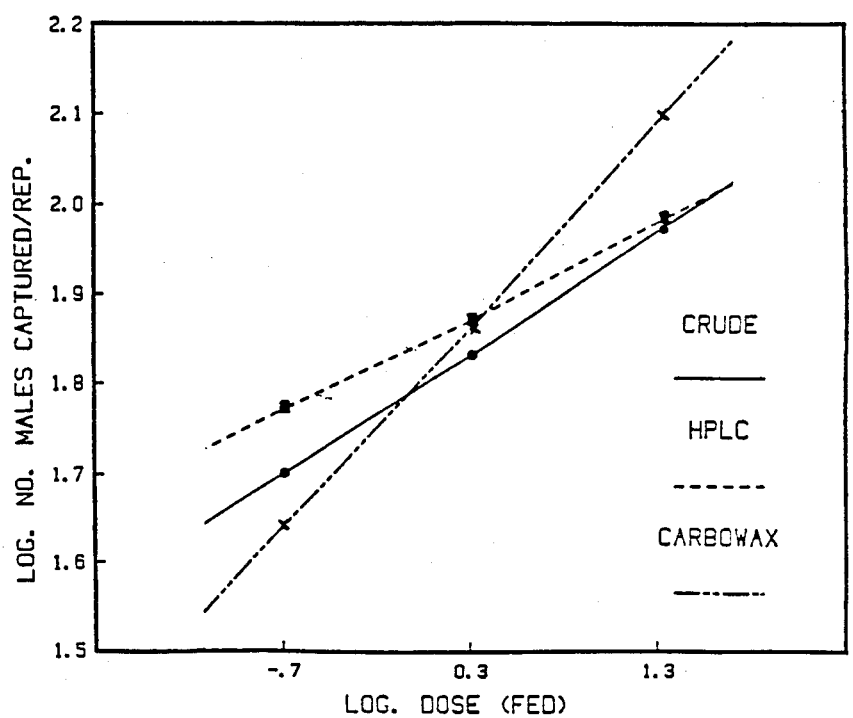

Further purification on a polar (Carbowax 20M) column yielded a single peak with KI=2200 that produced full activity in laboratory and field bioassays (FIGS. 2A and 2B). Quantitative analysis of this material indicated that a FED was equivalent to ca. 4 pg (4 pg=$4 \times 10^{-12}$ g=$1.4 \times 10^{-13}$ oz). The active peak from the Carbowax 20M column was found to be >99.8% pure when analyzed on the cyanopropyl methyl silicone, methyl silicone, polyethylene glycol, and cholesteryl-p-chlorocinnamate capillary columns as described in Example 1.

IDENTIFICATION OF THE ATTRACTANT

Identification of (Z)-3-dodecen-1-ol (E)-2-butenoate was particularly difficult because no precedent for this structure existed. Prior to the invention, this compound was not known. In addition, prior to the invention, no insect sex attractant compound was known which had a crotonate ester portion as part of the chemical structure, thus, there was no suggestion of a structural/functional relationship of the novel compound as an insect pheromone, in general, or specifically for the SPW. Structural elucidation of unknown chemical is exceptionally difficult because limited theoretical basis exists for predicting chemical structure from spectroscopic data. The relationships between spectral pattern and structure are not well understood theoretically in enough cases to permit structure assignment by theory alone.

In addition to lack of precedent of structure assignment, another difficulty in the identification of the compound was that only limited amounts (ca. $4 \times 10^{-6}$ g obtained after collecting 850,000 virgin female SPW hours) of the isolated compound were available, thus limiting investigations to use of gas chromatography/mass spectrometry (GC/MS) and nuclear magnetic resonance (NMR) spectroscopy which employed micro-analytical techniques developed by us.

Another difficulty in identification of (Z)-3-dodecen-1-ol (E)-2-butenoate was that a computer comparison of the mass spectrum or NMR spectrum against a file of reference spectra could not be carried out because there was no spectrum on file for the (E)-2- butenoate moiety. Additionally, in this case because of the novel structure of the compound, previously described methods of micro-analytical techniques used to determine the double bond position of the pheromone were ambiguous. To obtain final elucidation of the SPW sex attractant compound, 12 compounds, in addition to (Z)-3-dodecen-1-ol (E)-2-butenoate, which were all closely related in structure, were synthesized and tested. Of these compounds, five showed possible attractancy in the laboratory bioassay. These are (Z)-3-dodecen-1-ol (E)-2-butenoate, (E)-3-dodecen-1-ol (E)-2-butenoate, (Z)-2-dodecen-1-ol (E)-2-butenoate, (Z)-3-dodecen-1-ol (Z)-2-butenoate, and (Z)-4-dodecen-1-ol (E)-2-butenoate. The only compound which showed significant field response was (Z)-3-dodecen-1-ol (E)-2-butenoate.

Figure 3A:
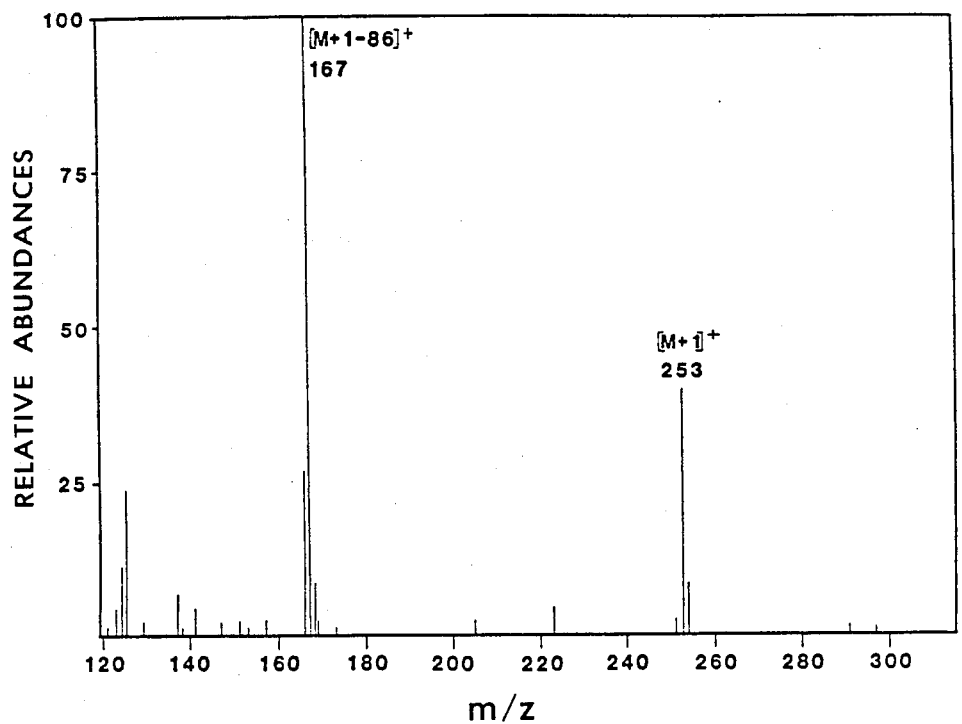
FIGS. 3A and 3B show the isobutane (A) and methane (B) ionization mass spectra of the active fraction from SPW female volatiles.
Figure 3B:
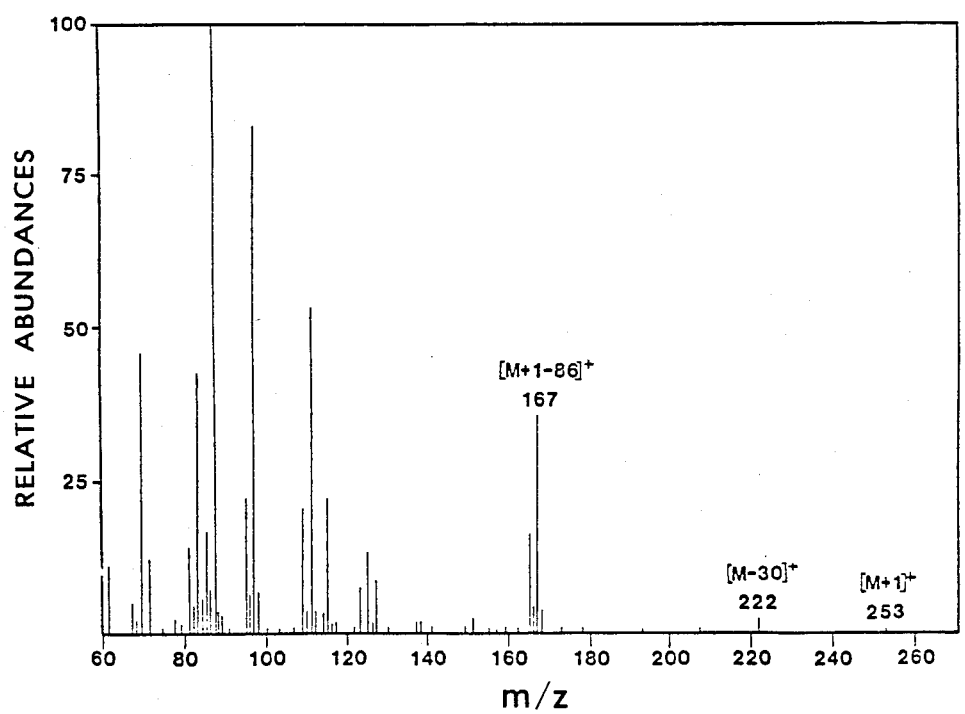

The following structural information was elucidated from the mass spectral data. The isobutane chemical ionization (CI) mass spectrum (FIG. 3A) established that the molecular weight of the sex attractant was 252 with diagnostic peaks at m/e 251 (M−1), 253 (M+1), 254 (M+2), and 291 (M+39). The fragment ion at m/e 167 (M+1-86) suggested the loss of butenoic acid ($C_4H_6O_2$) from the parent molecule. The methane CI mass spectrum (FIG. 3B) in addition to showing a peak at (M+1-86) provided a base peak at m/e 87 [$C_4H_7O_2^+$] consistent with protonated butenoic acid. Based on the mass spectral data the structure was proposed as a butenoate of a 12-carbon alcohol which contained one degree of unsaturation. Ozonolysis of the sex attractant (ca. 50 ng/ozonolysis) produced two major products that were identified as nonanal and decanal (1:0.8, respectively) by comparison of their retention times on a 50 m CW-20M capillary column and their mass spectra with synthetic standards.

Figure 4:
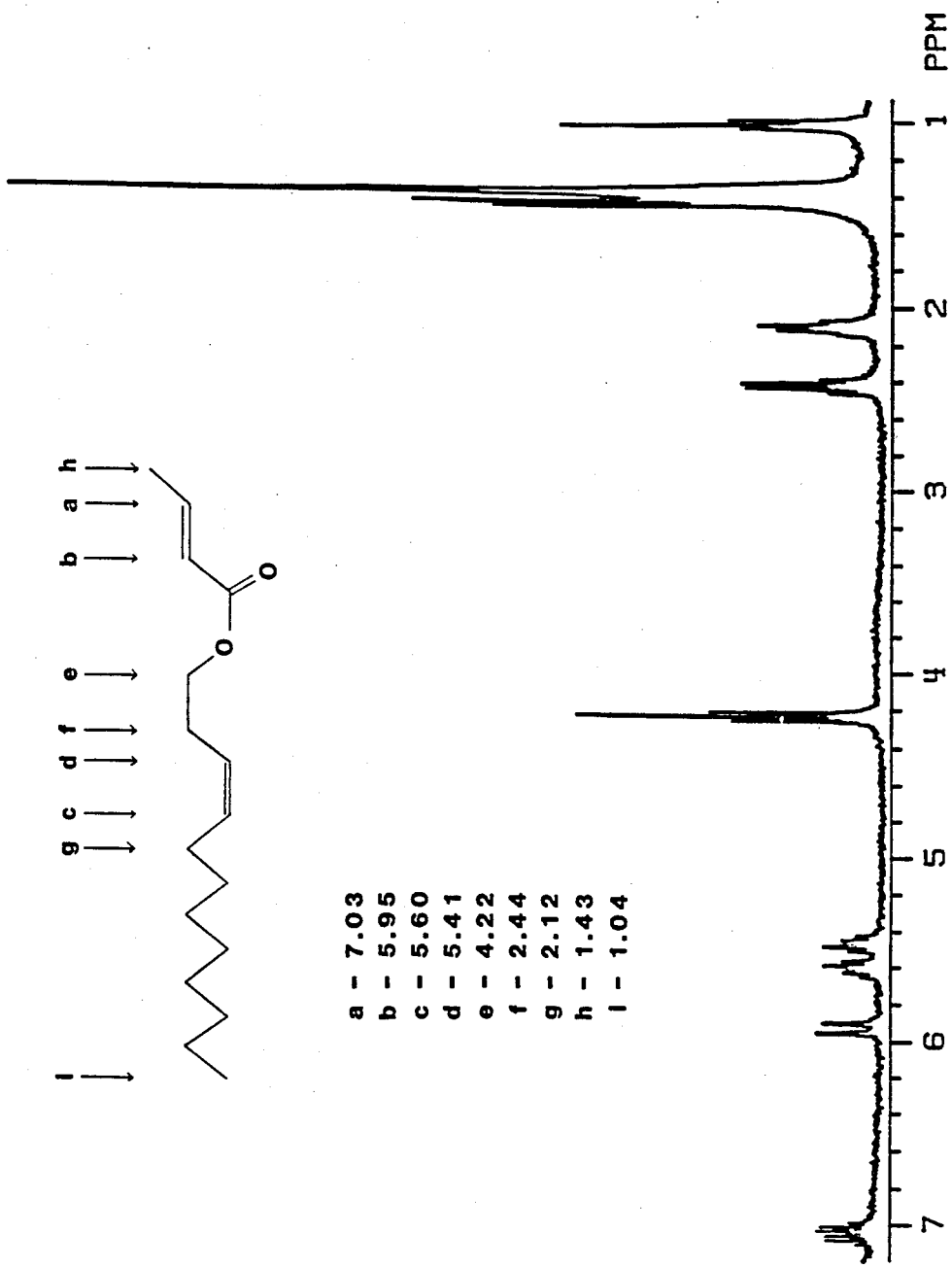
FIG. 4 shows the PMR spectrum of the purified natural sex attractant.

High-field 300 mHz PMR with decoupling experiments provided the following spectral information. Results obtained in PMR coupling experiments of the purified natural material are shown in Table 1. The spectrum (FIG. 4) indicated four olefinic protons. The proton giving rise to the signal at $\delta=7.03$ (1H sextet) was coupled to the olefinic proton at $\delta=5.95$ (1H, d) and the methyl protons of $\delta=1.43$ (3H, d). Thus the crotonate moiety, O=C—CH=CH—CH$_3$, was established. The olefinic proton $\delta=5.41$ (1H, m) was coupled to the methylene protons at $\delta=2.44$ (2H, q), which also were coupled to the methylene protons at $\delta=4.22$ (2H, t), CH=CH—CH$_2$—CH$_2$—O. Thus the position of the olefinic bond in the alcohol chain was unequivocally established as being in the three-position. The olefinic proton $\delta=5.60$ (1H, m) was coupled to the methylene protons at $\delta=2.12$ (2H, m) and the olefinic proton at 5.41 (1H, q). The methylene envelope $\delta=1.40$ (12H, m) and the methyl protons $\delta=1.05$ (3H, t) are consistent with a heptyl moiety. Examination of PMR spectra of synthetic samples of (Z)- and (E)-3-dodecen-1-ol and the methyl esters of (Z)-and (E)-2-butenoate indicated that the geometry of the olefinic bonds were (Z)-3-dodecen-1-ol (E)-2-butenoate.

TABLE 1

| Decoupler settings in PPM | PPM of α proton(s) |
|---|---|
| 7.03 | 5.95 (d → s)[b] + 1.43 (d → s) |
| 5.93 | 7.03 (m → q) |
| 5.60 | 2.12 (m → t) + 5.41 (−) |
| 5.41 | 2.44 (q → t) + 5.6 (−) |
| 4.22 | 2.44 (q → d) |
| 2.44 | 5.41 (m → d) + 4.22 (t → s) |
| 2.12 | 5.60 (m → d) |

[a]300 mHz.
[b]s = Singlet, d = doublet, t = triplet, m = multiplet, q = quartet, and (−) = not discernable due to decoupler splash.

In addition to (Z)-3-dodecen-1-ol (E)-2-butenoate, the other three possible geometric isomers were synthesized. All four isomeric forms were adequately resolved on a cyanopropyl methyl silicone capillary column. The isolated natural sex attractant had a retention time identical to that of the synthetic (Z)-3-dodecen-1-ol (E)-2-butenoate. The synthetic (Z)-3-dodecen-1-ol (E)-2-butenoate was 99+% pure and identical to the purified natural material by all analytical procedures.

PMR and capillary GC data established that only one compound identical to the synthetic (Z)-3-dodecen-1-ol (E)-2-butenoate had been isolated as the natural sex attractant. Ozonolysis of the synthetic sex attractant also produced the same two aldehyde products (nonanal and decanal) that were produced by ozonolysis of the natural sex attractant material.

USES OF THE ATTRACTANT

As previously discussed, the pure or substantially pure sex attractant compound may be used as a detecting agent, monitoring agent, or control agent for adult weevils. In practice, (Z)-3-dodecen-1-ol (E)-2-butenoate is used as a trap bait or is otherwise applied to a locus of the adults in an amount effective to induce the desired response. In the case of an attractant response, for example, an effective amount is defined as that quantity of compound which attracts weevil males to the location of a bait at a rate significantly higher than males are attracted to a nonbaited location. Under typical field conditions, amounts in excess of about $5.7\times10^{-12}$ g will be effective. Factors such as population density, temperature, wind velocity, and release rate will influence the actual number of weevils trapped.

In the case where the desired response is disruption of mating by confusing or inhibiting the weevil, an effective amount is defined as that quantity of compound which permeates the atmosphere such that males are prevented from orienting to and inseminating the females, i.e., disruption of mating, at a rate significantly higher than disruption of mating of males at a nontreated location. As with the attractant response, factors such as population density, temperature, wind velocity, and release rate will influence the actual number of weevils disrupted.

It is envisioned that (Z)-3-dodecen-1-ol (E)-2-butenoate would be effective in detecting, monitoring, or controlling SPW populations when used in conjunction with any type of trap or pheromone disseminator known in the art. Illustrative of the wide variety of traps or pheromone diseminators which may be used are the following: sticky trap, funnel trap, and pink bollworm trap. Typically, the compound would be applied to the release substrate in solution with a suitable carrier such as an organic solvent or undiluted. Volatilization can be retarded by inclusion of a higher molecular weight material to the (Z)-3-dodecen-1-ol (E)-2-butenoate solution. Slow release may also be effected by encapsulation or absorption into a porous substrate.

When used as a detection or monitoring agent, traps are baited with the novel compound of the invention and the catch tabulated to determine size and location of infestation. Economic use of appropriate pest management systems can then be determined.

Use of the sex attractant of the invention as a control agent can be carried out in several ways. One method is to use the compound to attract the insects to suitable substrates and subsequently or simultaneously expose the insects to insecticides which control the weevil. An effective amount of the insecticide is used, that is, an amount that is lethal for an exposed insect or at least sublethal but sufficient to incapacitate the insect in regard to mating activity. Illustrative of the wide variety of insecticides which may be used with the compound of the invention is endosulfan. Insecticides can be used in traps baited with the novel sex attractant of the invention. This eliminates the need to spread the insecticides unnecessarily and helps prevent killing useful insects and other animals.

A second method to control weevils using the novel compound is to detect the location and boundaries of localized weevil infestations and employ in the area biological control agents, e.g., parasites such as Microbracon, predators such as Argentine ants, and pathogens such as *Beauvaria globulifera*. As with the use of insecticides, this method eliminates the need to spread the control agents unnecessarily and minimizes adverse impact to useful insects and the environment.

(Z)-3-dodecen-1-ol (E)-2-butenoate may also be used to control weevils by confusion of SPW males, thus preventing mating. For example, one technique is to permeate the atmosphere with sufficient compound to prevent the males from orienting to and inseminating the females.

Other uses of the novel sex attractant will be obvious to those in the art.

EXAMPLES

The following examples are intended only to further illustrate the invention and are not intended to limit the scope of the invention which is defined by the claims.

EXAMPLE 1

Isolation of the Natural Sex Attractant

Sweetpotato Weevil Rearing and Handling. Insects were reared in the laboratory on commercially obtained sweet potatoes at 26±1° C. 60±5% RKH under a 14:10 (L:D) photoperiod using the procedures described by Coffelt et al., *Environmental Entomology* 7: 756–758 (1978). Virgin insects were obtained (females for sex attractant collection and males for use in bioassays) by separating male and female weevils within 24 hours of eclosion. Adults were maintained, prior to testing, for 5-7 days in groups of 50 to 75 in 100×15 mm glass Petri dishes with bottoms lined with Whatman #1 filter paper. During this period, males and females were kept in separate growth chambers with environmental parameters identical to those used for insect rearing. Adults were provided a small slice of sweet potato every 48 hours.

Collection of SPW Volatiles. Collections of SPW volatiles were made by drawing air over virgin female weevils that were confined in a 10.5-liter (24.5 cm×22.2 cm diameter) glass jar. Each jar contained 1500–2000 females and one sweet potato. The jars were kept in a laboratory hood within a room maintained at 26±1° C. and 65±5% RH and a 14:10 (L:D) photoperiod. Vacuum was used to pull ambient air through the unit at a rate of 2 liters/min. Volatiles emanating from the unit were entrained using two glass adsorption traps (1.5×8 cm) each containing 2.0 g of diatomaceous earth (60/80) mesh sold under the tradename Chromosorb 102 by Johns Manville. Prior to use the adsorbent was eluted with 100 ml of reagent grade diethyl ether.

Volatiles were collected continuously over a 30-day period for a given batch of insects. Sex attractant was collected at 48-hour intervals by eluting the entrained volatiles with 5–7 ml of pentane:ether (90:10). A fresh sweet potato was placed in the unit at this time. Approximately 850,000 female equivalent days (FED) were collected.

Isolation of Sex Attractant. Excess solvent was removed from the collected volatiles using heat (25° C.) and $N_2$. Next, the concentrate was chromatographed on a gravity-flow glass column (15 cm×1 cm i.d.) prepared by slurry packing 5.0 g of 60–100 mesh silica (J. T. Baker Chemical Co., Phillipsburg, NJ). Solvents used for the gravity flow column included 5% ether-hexane (80 ml) and 10% and 20% ether-hexane (80 ml each). The active fractions from the gravity flow column were concentrated and injected onto a HPLC column (250 mm×4.4 mm i.d.) packed with 5 μm silica (sold under the tradename Lichrosorb Si-60 by E. M. Laboratories, Inc.). The HPLC column was eluted with 2% ether in hexane at a flow rate of 2.0 ml/min. Ten fractions (2 ml each) were collected. An additional 20 ml of 5% ether-hexane was used to remove the (inactive) polar material from the column. The active fractions from the HPLC column were combined, concentrated, and further purified by GLC.

All micropreparative GLC was performed with a Varian Model 1400 gas chromatograph equipped with a flame-ionization detector. The effluent from the packed columns was split with 2% of the effluent routed to the detector, and 98% collected in a cooled, 30-cm glass capillary tube as described by Brownlee and Silverstein, *Analytical Chemistry* 40: 2077–2079 (1968).

The initial column used for further purification of the active material from HPLC was a 2 m×2.3 mm i.d. glass column packed with 5% methyl silicone (sold under the tradename OV-101 by Altech Assoc.) on 80–100 mesh diatomaceous earth (sold under the tradename Chromosorb G-HP by Johns Manville). Helium was used as the carrier gas at 20 ml/min and the column temperature was programmed from 120° to 220° C. at 10°/min. The active fraction collected from the OV-101 column was subsequently chromatographed on a 1.8 m×2.0 mm i.d. glass column packed with 4.4% polyethylene glycol (sold under the tradename Carbowax 20M by Altech Assoc.) on 120–140 mesh diatomaceous earth (sold under the tradename Chromosorb W by Johns Manville). Helium was used as the carrier gas at 20 ml/min and the column was operated isothermally at 180° C.

All analytical GLC was performed with a Hewlett-Packard Model 5790 gas chromatograph equipped with a flame ionization detector and a splitless capillary injector. Output from the detector was interfaced to a Nelson 4416 data system. The active fraction from the Carbowax packed column was analyzed on the following fused silica capillary columns: 50 m×0.25 mm i.d. methyl silicone sold under the tradename BP-1 by Scientific Glass Engineering; 50 m×0.25 mm i.d. Carbowax 20M; 50 m×0.25 mm i.d. cyanopropyl methyl silicone sold under the tradename CPS-1 by Quadrex Corp.; and a 35 m×0.25 mm i.d. soft glass column coated with cholesteryl-p-chlorocinnamate as described by Heath and Doolittle, *Journal of High Resolution Chromatography* 6: 16–19 (1983). Helium was used as the carrier gas for all columns at a linear flow of 18 cm/sec.

Identification. The active component was identified by chemical ionization mass spectrometry (CI-MS) and by Fourier transform proton nuclear magnetic resonance (FT-PMR). Additional structural information on the active compound was derived from the mass spectra of the products from microozonolysis.

Mass spectra were obtained with an upgraded Finnigan 1015/3200 chemical ionization mass spectrometer coupled with a Varian 1400 gas chromatograph and a user-designed splitless injector. Fused silica capillary columns used in the gas chromatographic inlet system included a 50 m×0.25 mm i.d. methyl silicone (BP-1) and a 50 m×0.25 i.d. Carbowax 20M (Quadrex) column. Helium was used as the carrier gas at a linear flow of 18 cm/sec. Reagent gas, either methane or isobutane, was introduced as make up gas. The PMR spectra were obtained with a Nicolet 300 mHZ Fourier transform spectrometer. Approximately 4 μg of the purified compound was placed in a 70 μl external capillary extension tube (Wilmad, Buena, NJ) containing 15 μl of deuterated benzene. Two thousand transients were collected over a 1-hour period using a 6 μsec pulse (90° tip angle). Proton decoupling was accomplished by using standard decoupling techniques (decoupler power ca. ½ watt) and 4000 transients spectra were obtained over a 2-hour period.

Microozonolysis of the sex attractant (50 ng each experiment) was carried out in carbon disulfide or hexane at −70° C. and the ozonide was reduced with triphenylphosphine according to the method described by Beroza and Bierl, *Analytical Chemistry* 38: 1131-1135 (1967). The ozonolysis products were analyzed by CI-MS. Synthetic standards were used to confirm the ozonolysis products and also to verify the spectral data.

Beginning with the crude material, and continuing through the purification, all materials were bioassayed in the laboratory to ensure no loss of activity occurred. In addition, field bioassays of the crude, HPLC, and GLC Carbowax samples were conducted to ensure that no loss of activity if the field occurred as a result of the separation performed. The bioassay procedures are described in Example 3. As shown in FIGS. 2A and 2B, no loss of biological activity relative to the crude material was noted either in the laboratory of the field bioassay. The regression data are significant at the 1% or 5% level.

Laboratory bioassays indicated all of the activity of the initial collections was recovered in the 5% ether-hexane eluant (80 ml) from the gravity flow silica column. No increase in activity was observed by the addition of the more polar components that were obtained by further elution with 10% and 20% ether-hexane. The active fractions from several gravity flow runs were combined and subsequently purified by HPLC. The biologically active fraction from HPLC eluted between a column capacity ratio (k') of 3.67 and 4.33.

EXAMPLE 2

Synthesis of (Z)-3-Dodecen-1-ol (E)-2-Butenoate

The synthesis of (Z)-3-dodecen-1-ol (E)-2-butenoate, I, shown in FIG. 1, was initiated with the preparation of 3-dodecyn-1-ol from 1 decyne.

For the synthesis of 3-dodecyn-1-ol, II, n-butyllithium (9.3 ml of 2.7M in hexane) was injected into a cooled solution (≦0° C.) of 1-decyne (4.5 ml, 25 mmole) in dry tetrahydrofuran (THF, 36 ml) under nitrogen. Ethylene oxide (1.5 ml, 30 mmole) was injected from a precooled syringe, and then hexamethylphosphoric triamide (9 ml, ca. 2 equiv.) was injected. The resulting mixture was stirred overnight at ambient temperature and then worked up by dilution with water and extraction with hexane. The product alcohol was distilled under reduced pressure to give 3.45 g (77.5%): b.p. 74°-79° C./0.05 mm; IR (CCl$_4$) 3640 cm$^{-1}$; NMR δ 0.88 (3H, t, CH$_3$), 1.27 (CH$_2$ envelope), 2.18 (2H, m, CH$_2$CHC≡C), 2.41 (2H, m, HOCH$_2$CH$_2$C≡C), 3.67 (2H, m, CH$_2$OH) ppm.

To synthesize (Z)-3-Dodecen-1-ol, III, alkynol II (3.25 g, 17.9 mmole) was hydrogenated over 30 mg of Lindlar catalyst prepared according to Mozingo, *Organic Syntheses* 3: 685-690 (1955). The reduction was carried out in pentane (35 ml) at atmospheric pressure and ambient temperature. The reduction was monitored by gas chromatography using 25-m (0.25 mm i.d.) fused silica capillary column coated with CPS-1 (Quadrex Corporation). After filtration and concentration, the alkenol III was distilled under reduced pressure to give 2.87 g (88.3%): b.p. 67°-70° C./0.05 mm, IR (CCl$_4$) 3300 broad, 1050 cm$^{-1}$; NMR δ 0.88 (3H, t, CH$_3$) 1.27 (CH$_2$ envelope), 2.05 (2H, m, CH$_2$C=C), 2.33 (2H, m, HOCH$_2$CH$_2$C≡C), 3.64 (2H, m, CH$_2$OH), 5.38, 5.55 (2H, m's, cis olefinic H).

To synthesize (Z)-3-Dodecen-1-ol (E)-2-butenoate, I, crotonyl chloride (5.7 ml of 90% technical grade, 59.4 mmole) and alkenol III (8.75 g, 47.5 mmole) were dissolved in methylene chloride (CH$_2$Cl$_2$, 90 ml) and cooled in an ice bath. Pyridine (3.8 ml, 47.5 mmole) was added in CH$_2$Cl$_2$ (10 ml) dropwise. The resulting mixture was stirred cold for 1 hour and then worked up with water and CH$_2$Cl$_2$. The organic phase was dried (MgSO$_4$) and concentrated. The yield of crude ester (12.0 g) was nearly quantitative. Distillation of 6.0 g of crude product under reduced pressure gave 5.1 g (84%) of I containing less than 10% of the isomeric 3-butenoate ester: b.p. 105°-109° C./0.1 mm; IR (CCl$_4$) 1720 (C=O), 1660 (C=C) and 970 cm−1 (trans HC=CH).

The distilled synthetic material was purified on a 5 μm silica gel HPLC column (25 cm×4.4 mm i.d.) using 2% ether:98% hexane. This HPLC purified material was then further purified using a 20% AgNO$_3$ silica gel HPLC column, 25 cm×1.25 cm o.d., and was eluted with toluene. This material was analyzed by capillary GC on the same columns described above.

EXAMPLE 3

Sex Attractancy of the Natural and Synthetic Material

Quantitative bioassays comparing the attractive properties toward the SPW of various preparations of natural and synthetic sex attractant were conducted in the laboratory and the field on SPW males reared by the procedure described in Example 1.

Laboratory Bioassay. Samples were bioassayed using the procedure described by Coffelt et al., supra. Briefly, 3-5 μl of test extract were pipetted onto the flattened end of a glass rod and then exposed to a series of ten males that were held individually in 1.6×5-cm Teflon coated shell vials. The treated rod was suspended within 1 cm of the test insect for a period not greater than 15 seconds. A positive response, defined as antennal elevation and locomotion, was taken as evidence of the presence of sex attractant. Rods treated with solvent only served as controls and exposure of a single rod to ten males constituted one replication. This bioassay was employed only after initial studies revealed that only those fractions that elicited the above responses were attractive to males in the field. All laboratory bioassays were conducted under Cool-White fluorescent room lighting at 26±2° C. during the latter ½ of the photophase using males that were between 7 and 30 days of age. Sex attractant units are expressed in terms of FED; one FED being the estimated quantity of sex attractant obtained from one female per 24-hour period. The collected volatile material and all fractions obtained in the purification of the sex attractant were bioassayed at $10^{-1}$, $10^{-2}$, $10^{-3}$, and $10^{-4}$ FED.

Field tests. Field bioassays were conducted in February-August in 0.2-ha plots of sweet potato at the Federal Experiment Station, St. Croix, U.S. Virgin Islands.

In the first series of tests (February), unpurified volatiles that contained sex attractant, partially purified material (active fractions from HPLC) and purified material (from the Carbowax 20M GC column) were compared to determine whether any loss of attractiveness to feral males occurred as a consequence of the indicated fractionations.

Doses of 0.0, 0.2, 2.0, and 20 FED in 50 μl hexane were applied to 22×22-mm glass cover slides. After solvent evaporation, the cover slides were placed in the center of a 100×15-mm Teflon-lined Petri dish (cover slides elevated 16 mm above floor of dish). Dishes were placed at the center of individual 50×50-cm wooden platforms with the height of the platform being approximately equal to the plant canopy height (15-20 cm). The number of males on the platform and in the dish (<15 mm from source) within 5 minutes of deployment of the sample were recorded and taken as evidence of response. All tests were conducted between 1930 and 2145 h Atlantic ST at temperatures ranging from 20.5°-22.2° C.

Platforms were deployed at 2-m intervals in a line approximately perpendicular to the prevailing easterly wind direction. Treatment locations were randomized within plots, and a total of nine replications were made in three different plots over several nights with no plot being used for more than one replication per night. Cover slides treated with hexane only served as controls.

The second series of field bioassays was conducted in March and September to compare the relative attractiveness of the purified natural product with synthetic pheromone (>99% purity). Doses tested were 0.0, 0.08, 0.8, 8.0, and 80 ng/50 µl; the material was formulated on glass slides. Additionally, the purified natural material was compared with synthetic pheromone when formulated on rubber septa (A. H. Thomas #8753-D22). The material was dissolved in 100 ml of hexane and pipetted into the large reservoir of the septum cap. Septa were loaded with 10, 30, 100, and 300 ng of material and aged a minimum of 2 days prior to use. Septa treated with hexane served as controls. Septa were positioned about 3 cm above the floor of the Petri dish with a paper clip. Test duration was 20 minutes. There were four replications at each dose in two different plots on different days. Within plots, treatment locations were randomized between replications. Treatments were randomized within plots and two plots were used. Other parameters were as in the previously described field bioassay.

The third series of field bioassays was conducted in August to identify the nature of the relationship between the applied dose of synthetic sex attractant (>99% purity) and the number of feral males attracted. Bioassays were carried out as described above. The sex attractant was formulated on rubber septa in doses of 0, 1, 10, 100, and 1000 ng (eight replications).

Figure 5A:
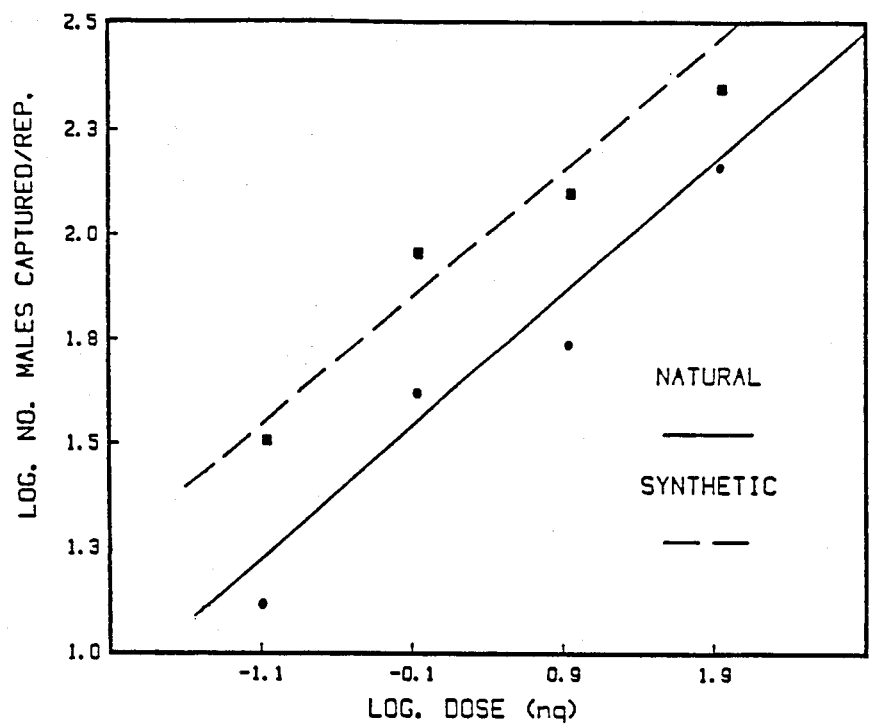
FIGS. 5A and 5B show the field response of SPW males to the purified natural sex attractant and synthetic sex attractant on glass (A) and rubber septa (B).
Figure 5B:
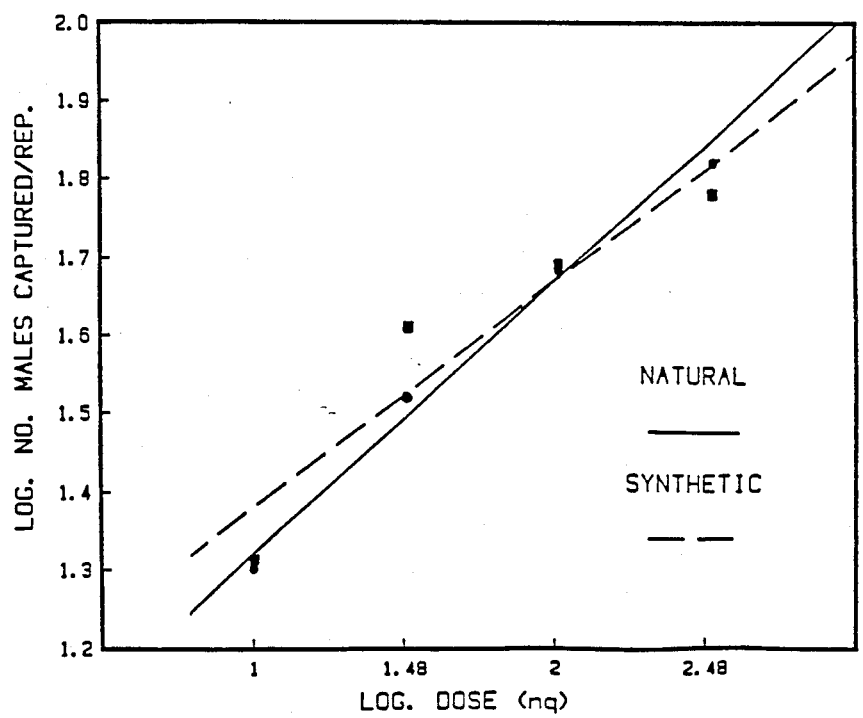
Figure 6:
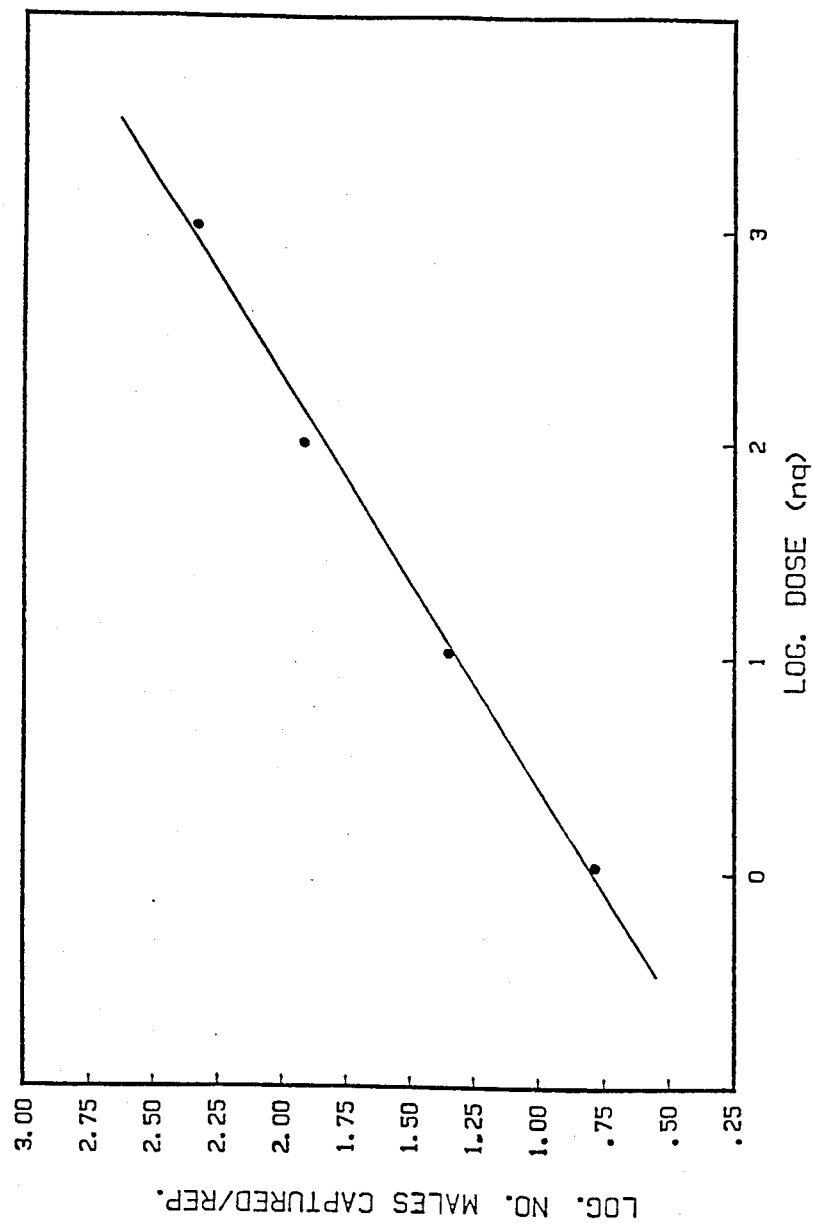
FIG. 6 shows the field response of SPW males to (Z)-3-dodecen-1-ol (E)-2-butenoate in rubber septa.

The results of the laboratory study comparing the relative activity of the purified natural product and the synthetic material (six to ten replications at four different dosages for each material) indicated that there was no measurable difference between the two materials. The relative activity, in terms of male attraction in the field, is shown in FIG. 5. Two release substrates, glass (FIG. 5A) and rubber (FIG. 5B), were used and the similarity in response is shown in the figures. The dose-response of SPW males to (Z)-3-dodecen-1-ol (E)-2-butenoate formulated in rubber septa (eight replicates/point) is shown in FIG. 6. Controls did not capture a significant number of sweetpotato weevils in any test.

EXAMPLE 4

Field Tests

The attractive properties toward the SPW of the synthetic compound prepared as described in Example 2 under field conditions was tested in St. Croix, U.S.V.I. The numbers of sweetpotato weevils caught using a light trap, one sweetpotato weevil female, three females, and septa loaded with 100 ng or 10 µg of the synthetic sex attractant compound were compared. When females served as bait, they were held in a tetrahedral cage made from fiberglass. The synthetic compound was dissolved in hexane prior to application to the rubber septa. In a 24-hour test, traps baited with 100 ng or 10 µg of synthetic compound captured 75 and 275 males, respectively. For comparison the light trap captured two males (plus one female) and traps baited with one or three females captured two and five males, respectively.

The effectiveness of nine different types of traps baited with the synthetic compound prepared as described in Example 2 was evaluated under field conditions in St. Croix, U.S.V.I. The trap types used were light trap; sticky trap; water trap; PFT-1 (a plastic funnel live trap used for monitoring the pink bollworm, set within a truncated cone made from standard hardware cloth); PFT-2 (trap similar to PFT-1 but with larger entrance holes); black trap (similar to PFT-1 except truncated cone was painted black); yellow trap (similar to PFT-1 but with a yellow base); orange trap (similar to PFT-1 but with an orange base); and AFT (similar to PFT-1 but with an aluminum funnel).

Table 2 shows the number of males trapped per night (back transformation of $\sqrt{Y}\pm 0.05$) and trap ranking with AFT trap equalling 1.00.

TABLE 2

| Trap | Trap Comparison[a] | | | | Trap[b] rank |
|---|---|---|---|---|---|
| | 1 | 2 | 3 | 4 | |
| Light | | | 21a | 2a | 0.06 |
| Sticky | 94 | | | | 0.14 |
| Orange | 210 | 46 | | | 0.28 |
| Yellow | 196 | 45 | | | 0.29 |
| Black | | 40 | | | 0.24 |
| Water | | 46 | | | 0.27 |
| PFT-1 | | 81 | 107ab | 48b | 0.43 |
| PFT-2 | | | 347b | 137c | 0.94 |
| AFT | | | | 141c | 1.00 |
| N | 5 | 15 | 9 | 14 | |
| P for F test | <0.1 | <0.1 | <0.025 | <0.001 | |

[a]Means followed by the same letter were not significantly different (P < 0.05).
[b]Ranking from non-transformed means.

It is understood that the foregoing detailed description is given merely by way of illustration and that modification and variations may be made therein without departing from th (R)spirit and scope of the invention.

Having thus described the invention, we claim:

1. The substantially pure compound (Z)-3-dodecen-1-ol (E)-2-butenoate.

2. A sex attractant composition for the sweetpotato weevil, which comprises an effective attractant amount of the substantially pure compound (Z)-3-dodecen-1-ol (E)-2-butenoate and a carrier.

3. The attractant composition of claim 2 in combination with an effective amount of a control agent for the sweetpotato weevil.

4. The attractant composition of claim 3 wherein said control agent is an insecticide for the sweetpotato weevil.

5. A method of attracting adult male sweetpotato weevils, comprising applying to the locus thereof an effective attractant amount of (Z)-3-dodecen-1-ol (E)-2-butenoate.

6. The method of claim 5 wherein said (Z)-3-dodecen-1-ol (E)-2-butenoate is in combination with a suitable carrier therefore.

7. The method of claim 5 wherein (Z)-3-dodecen-1-ol (E)-2-butenoate is in combination with an effective amount of a control agent for the sweetpotato weevil.

8. The method of claim 7 wherein said control agent is an insecticide for the sweetpotato weevil.

9. A method of disruption of mating of adult sweetpotato weevils comprising applying to the locus thereof an effective disruptant amount of (Z)-3-dodecen-1-ol (E)-2-butenoate.

* * * * *